(12) United States Patent
Mita et al.

(10) Patent No.: US 7,469,607 B2
(45) Date of Patent: Dec. 30, 2008

(54) SAMPLING NEEDLE AND SAMPLE INJECTION APPARATUS

(75) Inventors: Masashi Mita, Tokyo (JP); Kazuhiko Mibayashi, Kyoto (JP); Osamu Shirota, Yokohama (JP)

(73) Assignee: Shiseido Company, Ltd., Tokyo (JP)

( * ) Notice: Subject to any disclaimer, the term of this patent is extended or adjusted under 35 U.S.C. 154(b) by 434 days.

(21) Appl. No.: 11/272,074

(22) Filed: Nov. 14, 2005

(65) Prior Publication Data

US 2006/0107771 A1    May 25, 2006

(30) Foreign Application Priority Data

Nov. 16, 2004    (JP) .............................. 2004-331987

(51) Int. Cl.
*G01N 1/10* (2006.01)

(52) U.S. Cl. .............. 73/864.87; 73/864.83; 73/864.91; 600/576; 600/580

(58) Field of Classification Search ................. 73/23.41, 73/61.55, 864.81–864.91; 600/576, 580
See application file for complete search history.

(56) References Cited

U.S. PATENT DOCUMENTS 4,240,429 A * 12/1980 Shackelford ............. 73/864.87

FOREIGN PATENT DOCUMENTS

JP        11-304779        11/1999

* cited by examiner

*Primary Examiner*—David A. Rogers
(74) *Attorney, Agent, or Firm*—IPUSA, PLLC (57) ABSTRACT

A sampling needle is disclosed that includes a sampling part that is inserted into a sample, and a sample holding part that holds the sample that is introduced through the sampling part. The sampling part and the sample holding part are arranged into a seamless structure, and the inner diameter of the sampling part and the inner diameter of the sample holding part are equal.

3 Claims, 6 Drawing Sheets

SAMPLING NEEDLE AND SAMPLE INJECTION APPARATUS

BACKGROUND OF THE INVENTION

1. Field of the Invention

The present invention relates to a sampling needle and a sample injection apparatus for temporarily storing a sample and supplying the sample to a predetermined receiving unit.

2. Description of the Related Art

Figure 1:
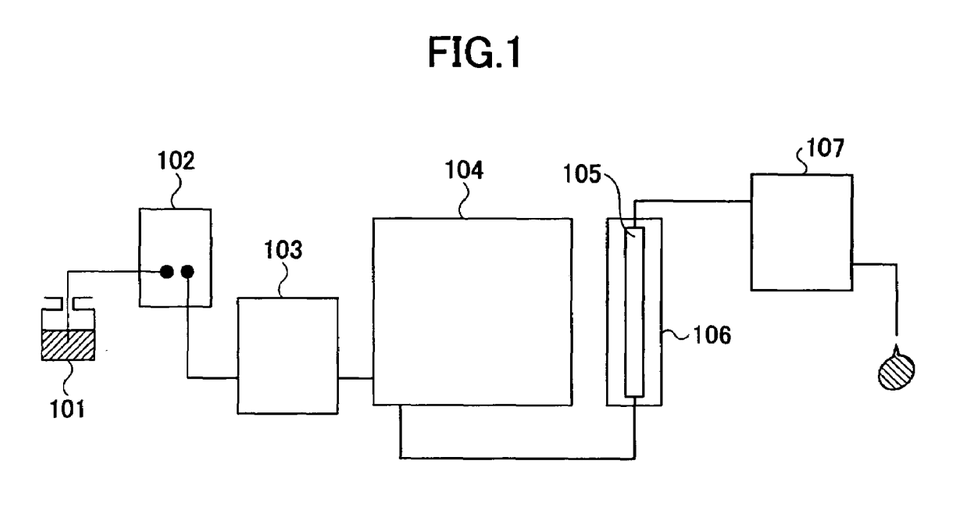
FIG. 1 is a diagram showing an exemplary configuration of a chromatography apparatus.

A liquid chromatography apparatus is widely used as chemical analyzing means for separating and determining the quantity of a chemical substance. FIG. 1 is a diagram showing a basic configuration of a liquid chromatography apparatus.

The liquid chromatography apparatus shown in this drawing includes a mobile phase reservoir 101 for storing liquid corresponding to a mobile phase, a mobile phase degassing unit 102 for removing air from the liquid (mobile phase), a pump 103 for sending the liquid (mobile phase) from the mobile phase reservoir 101 to a detector 107, an (auto) sample injection apparatus 104 for injecting a sample into the liquid (mobile phase) that is moving toward a separation column 105, the separation column 105 that is filled with a packing material for separating components of the sample, a column oven 106 for maintaining the separation column 105 at a substantially constant temperature, and the detector 107 that detects diffused components of the sample, for example.

In recent years and continuing, improvements in detection sensitivity of liquid chromatography are in demand, and in turn, measures are being implemented to increase the sensitivity of the liquid chromatography apparatus. However, as the sensitivity of the liquid chromatography apparatus is increased, the so-called carry-over becomes a problem.

Carry-over refers to an effect in which a substance of a sample previously measured remains in the liquid chromatography apparatus so that the remaining substance is detected in a current measurement, thereby falsely indicating that it is a component of the sample currently being measured. Such an effect may degrade the reliability of the analysis result. When a sample is injected into a liquid corresponding to the mobile phase by the auto sample injection apparatus 104, the sample may remain in the auto sample injection apparatus 104. The remaining sample may be introduced into the liquid chromatography analyzing system when a next sample is injected, and in this way carry-over may occur.

The occurrence of carry-over may be reduced by removing the sample remaining in the auto sample injection apparatus 104. In turn, research is being conducted to determine the position at which the sample remains within the auto sample injection apparatus 104.

In the auto sample injection apparatus 104, a sampling needle 110 (see FIG. 2) extracts a sample from a sample solution supplied in a sample container, and the sampling needle 110 extracting this sample is inserted into an injection port of an injection valve so that the sample inserted into the injection port may be transported to the separation column 105 by a flow path switching operation performed by the injection valve.

Figure 2:
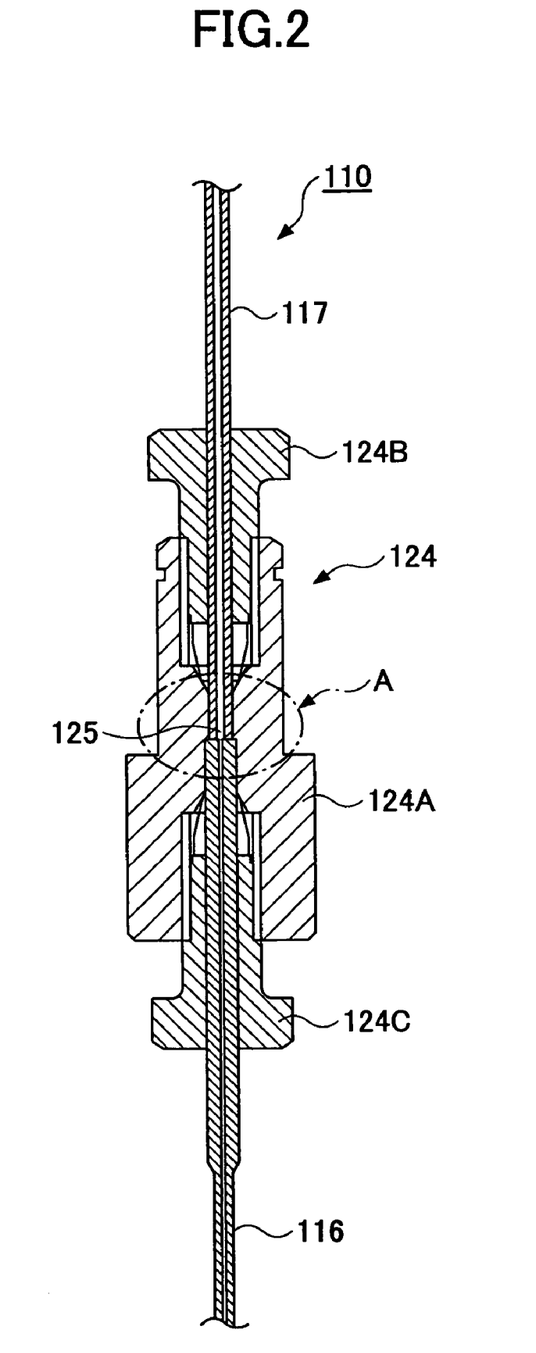
FIG. 2 is a cross-sectional view of a sampling needle that is used in the chromatography apparatus shown in FIG. 1.

The outer wall of the sampling needle 110, the injection port into which the sample is injected, and the flow path of the sample within the injection valve may be examples of locations at which the sample may remain within the auto sample injection apparatus 104. In turn, for example, Japanese Laid-Open Patent Publication No. 11-304779 discloses a technique for cleaning a portion or all of the locations at which the sample may remain within the auto sample injection apparatus so as to reduce the occurrence of carry-over.

The inventors of the present invention performed the following test using a liquid chromatography apparatus including the auto sample injection apparatus 104. First, a sample solution was injected into the liquid chromatography apparatus and a detection process was performed. Then, a cleaning process was performed on all the locations at which the sample may remain within the sample injection apparatus 104. Then, a blank sample solution (mobile phase) was injected using the auto sample injection apparatus 104 and a determination was made as to whether traces of the first sample solution remaining within the auto sample injection apparatus 104 could be found.

Figure 4:
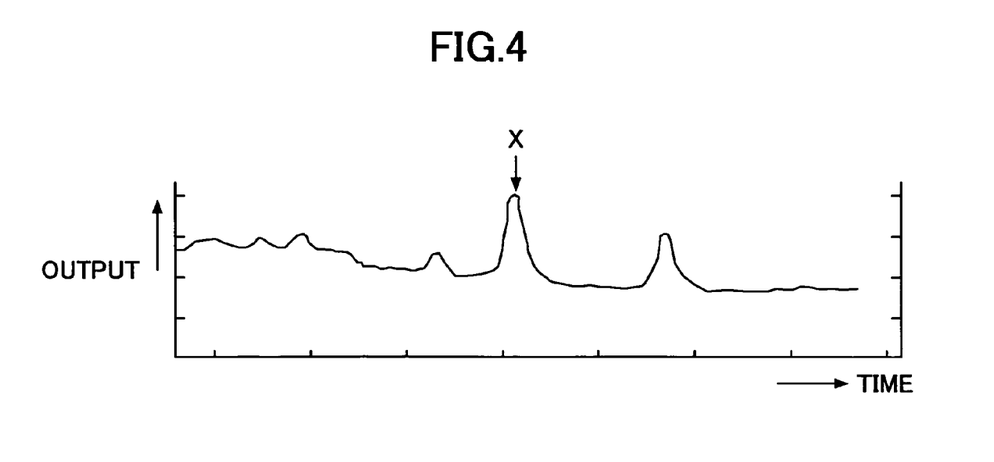
FIG. 4 is a graph illustrating the occurrence of carry-over in a case where the sampling needle of FIG. 2 is used.

FIG. 4 shows a chromatogram obtained from performing the above test. As can be appreciated from this drawing, even when a cleaning process was performed on all locations at which the sample may remain within the sample injection apparatus 104, a carry-over peak occurred as is indicated by the arrow X in the drawing. Therefore, a more reliable method for preventing carry-over is required.

SUMMARY OF THE INVENTION

The present invention has been conceived in response to one or more of the above problems, and it provides a sampling needle and a sample injection apparatus for effectively preventing the occurrence of carry-over.

According to one embodiment, the present invention provides a sampling needle that includes:

a sampling part that is inserted into a sample; and a sample holding part that holds the sample introduced through the sampling part;

wherein the sampling part and the sample holding part are arranged into a seamless structure; and an inner diameter of the sampling part and an inner diameter of the sample holding part are equal.

In a preferred embodiment, the sampling part and the sample holding part are integrally arranged into a seamless tube.

In another preferred embodiment, the sample holding part includes an attaching part that is fixed to an external apparatus, and a flexible part that is configured to flexibly deform, the external diameter of the flexible part being smaller than the external diameter of the attaching part.

According to another aspect of the present invention, a sample injection apparatus is provided that is used in a testing apparatus and is configured to automatically inject a sample into the testing apparatus, the sample injection apparatus including:

a sampling needle that includes a sampling part that is inserted into a sample, and a sample holding part that holds the sample that is introduced through the sampling part;

wherein the sampling part and the sample holding part are arranged into a seamless structure; and an inner diameter of the sampling part and an inner diameter of the sample holding part are equal.

DETAILED DESCRIPTION OF THE PREFERRED EMBODIMENTS

In the following, preferred embodiments of the present invention are described with reference to the accompanying drawings.

Figure 5:
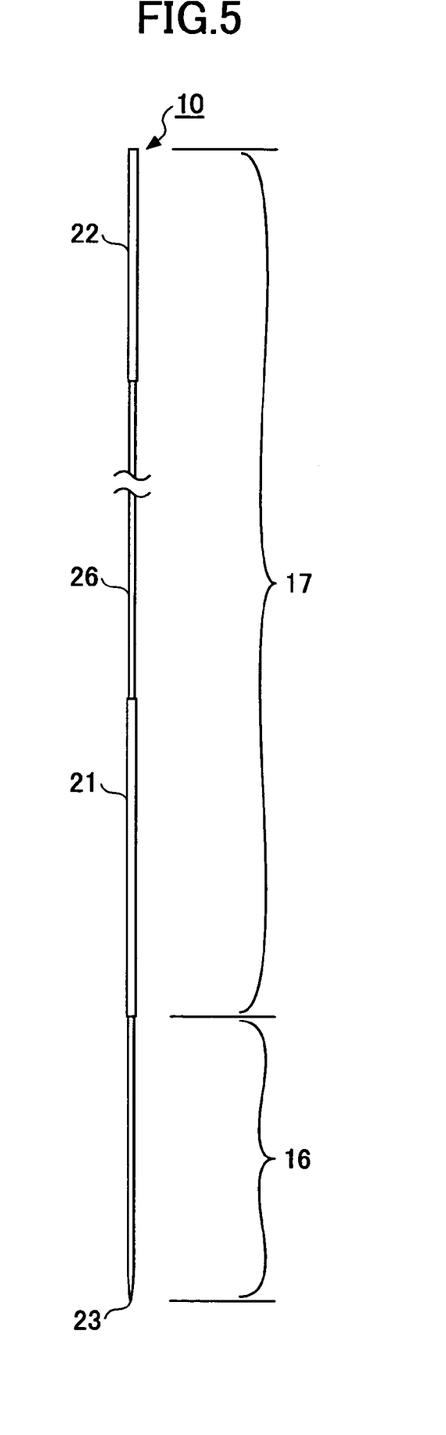
FIG. 5 is a diagram showing a configuration of a sampling needle according to an embodiment of the present invention.
Figure 6:
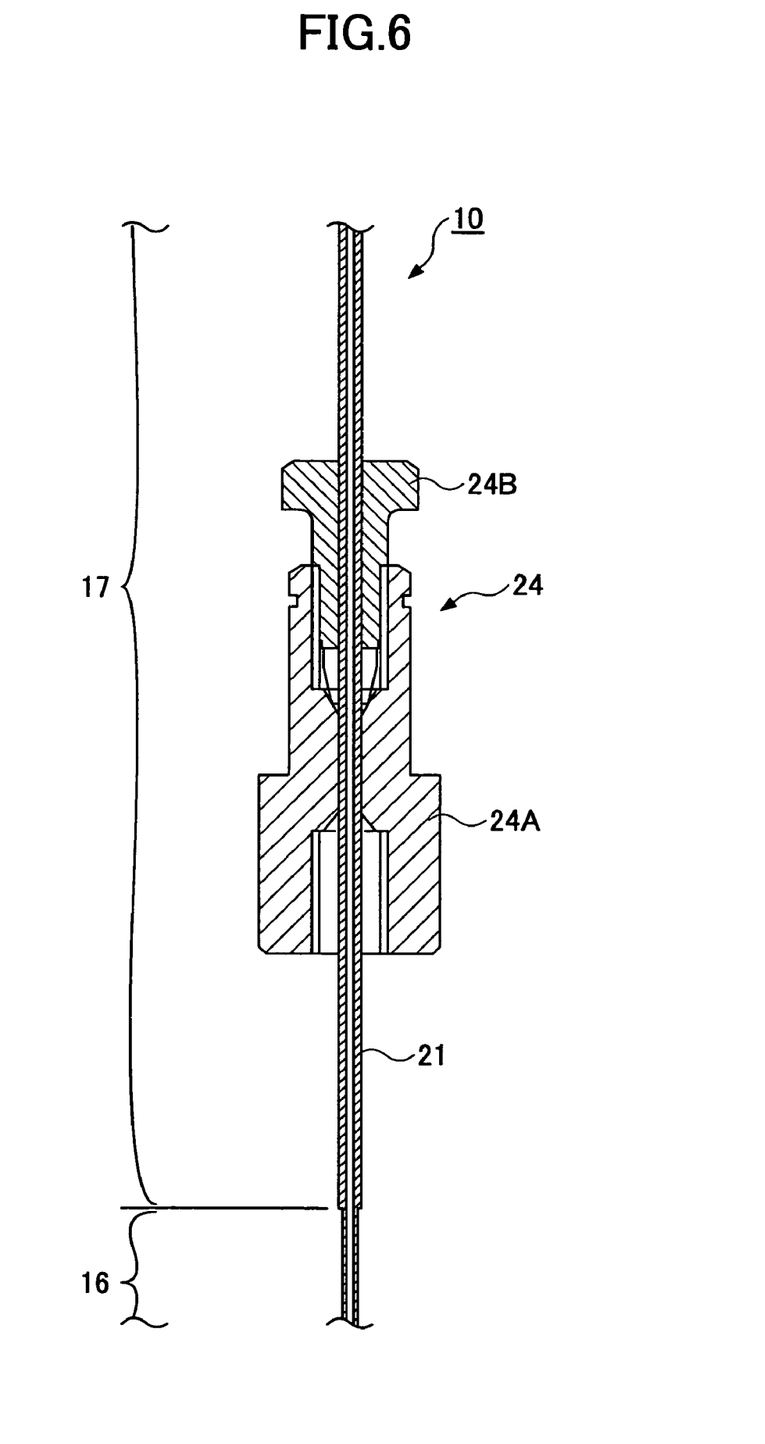
FIG. 6 is an enlarged cross-sectional view of a portion of the sampling needle of FIG. 5 at which a holder is attached.
Figure 7:
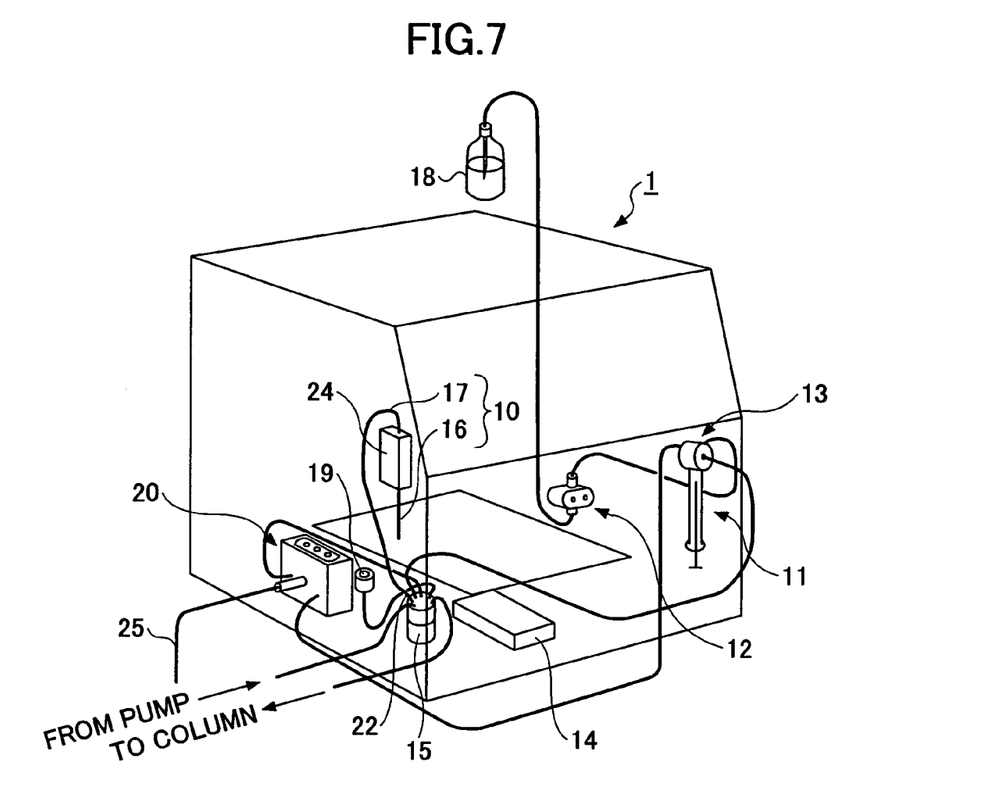
FIG. 7 is a diagram illustrating an exemplary configuration of a sample injection apparatus that uses the sampling needle shown in FIG. 5.

FIGS. 5 and 6 are diagrams illustrating a sampling needle 10 according to an embodiment of the present invention, and FIG. 7 is a diagram illustrating a sample injection apparatus 1 according to an embodiment of the present invention.

In the following, the configuration of the sample injection apparatus 1 is described.

As is shown in FIG. 7, the sample injection apparatus 1 includes the sampling needle 10, a syringe 11, a cleaning liquid pump 12, a valve 13, a sample container 14, an injection valve 15, a cleaning liquid container 18, a cleaning liquid port 20, and a needle moving mechanism (not shown), for example.

It is noted that the sample injection apparatus 1 may be used in place of the sample injection apparatus 104 in the liquid chromatography apparatus shown in FIG. 1, for example. That is, a liquid chromatography apparatus according to an embodiment of the present invention may have a configuration identical to that shown in FIG. 1 except for the features of the sample injection apparatus 1 and the sampling needle 11, and thereby, descriptions of other components of the liquid chromatography apparatus according to the present embodiment are omitted. However, the present invention is not limited to the above example, and other applications of a sampling needle and a sample injection apparatus are possible as well.

In the sample injection apparatus 1 shown in FIG. 7, the sampling needle 10 is connected to the syringe 11 via the valve 13. A sample stored in the sample container 14 may be introduced into or discharged out of the sampling needle 10 by a suction force created by the pushing or pulling of the syringe 11, for example.

The cleaning liquid container 18 is configured to store a cleaning liquid and is connected to the cleaning liquid pump 12. The cleaning liquid stored in the cleaning liquid container 18 may be suctioned by the cleaning liquid pump 12 to be transported to the valve 13 by pressure.

The valve 13 is arranged between the sampling needle 10 and the syringe 11. By switching the valve 13, the cleaning liquid pumped out of the cleaning liquid container 18 by the cleaning liquid pump 12 may be selectively supplied to the cleaning port 20 or the sampling needle 10. The cleaning liquid may be continually supplied to the cleaning port 20, and when the amount of cleaning liquid in the cleaning port 20 exceeds a predetermined amount, the cleaning liquid may be discharged through a drain 25 as waste liquid.

The injection valve 15 is arranged such that the sampling needle 10 may be inserted therein and includes an injection port 19 into which the sample or the cleaning liquid from the sampling needle 10 may be injected. Also, the injection valve 15 is configured to receive a liquid that is supplied thereto from outside the sample injection apparatus 1, and send the liquid out of the sample injection apparatus 1.

More specifically, when the sample injection apparatus 1 is used in a liquid chromatography apparatus, a solvent corresponding to the mobile phase is supplied to the injection valve 15 by a pump provided outside the sample injection apparatus 1, after which the solvent is sent to a separation column.

In one embodiment, the injection valve 15 includes six ports, and by switching the connection of the six ports, each of the flow paths connected to the six ports may be cleaned by the cleaning liquid (i.e., the solvent as the mobile phase). Also, a sample injected into the injection valve 15 from the sampling needle 10 may be sent to the separation column so that the components of the sample may be separated and analyzed.

Figure 3:
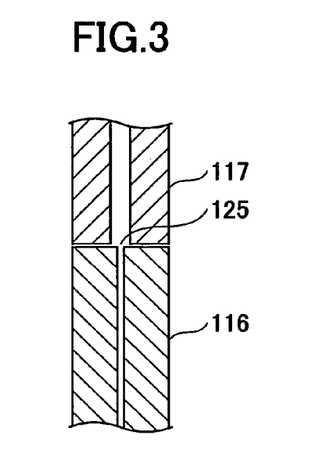
FIG. 3 is an enlarged cross-sectional view of a portion of the sampling needle shown in FIG. 2.

In the following, the sampling needle 10 according to an embodiment of the present invention is described. However, for the sake of convenience, first, a configuration of the sampling needle 110 as a comparison example as is shown in FIGS. 2 and 3 is described before describing the sampling needle 10 according to the present invention. It is noted that FIG. 3 is an enlarged view of a portion of the sampling needle 110 indicated by arrow A in FIG. 2.

The inventors of the present invention carefully examined the sampling needle 110 to look into the causes of the occurrence of carry-over. Through such examination, the following findings were made. A sampling part 116 and a sample holding part 117 of the sampling needle 110 are separate members that are connected at the portion indicated by the arrow A in FIG. 2. It is noted that the sampling needle 110 also includes a holder 124 for connecting the sampling needle 110 to a needle moving mechanism. The holder 124 includes a main body part 124A and screw parts 124B and 124C.

Looking further into the structures of the sampling part 116 and the sample holding part 117, as is shown in FIG. 3, the inner diameter of the sampling part 116 and the inner diameter of the sample holding part 117 are arranged to be different, and therefore, a stepped portion 125 is created at the connection point between the sampling part 116 and the sample holding part 117. In a case where such a stepped portion 125 is created at the connection point between the sampling part 116 and the sample holding part 117, when a sample is introduced into and discharged out of the sampling needle 110, the sample may not flow smoothly into the sampling part 116 upon discharging the sample owing to the existence of the stepped portion 125, and part of the sample may remain at the stepped portion 125.

When the sample remains within the sampling needle 110 as is described above, in a next measuring process, the sample remaining in the sampling needle may be sent to a measuring apparatus (liquid chromatography apparatus) to thereby cause carry-over.

Accordingly, in order to prevent carry-over, the sampling needle 10 according to an embodiment of the present invention is configured such that a sample may be prevented from remaining within the sampling needle 10. In the following, detailed descriptions of the configuration of the sampling needle 10 are given. FIG. 5 is a diagram illustrating an overall configuration of the sampling needle 10, and FIG. 6 is an enlarged cross-sectional view of an attaching part 21 of the sampling needle 10 and its vicinity.

The sampling needle 10 according to the present embodiment is a fine hollow tube that includes a sampling part 16 and a sample holding part 17. A sample (or mobile phase) may be introduced into the sampling part 16 through suction when the sampling part 16 is inserted into the sample (or mobile phase). Also, the sample (or mobile phase) introduced into the sampling part 16 may be injected into the injection port 19 when the sampling part is inserted into the injection port 19. A tip portion 23 of the sampling part 16 may be arranged into a circular cone shape. In one preferred embodiment, the apex angle of this circular cone shape may be 15 degrees, for example.

The sample holding part 17 is configured to temporarily hold the sample (or mobile phase) introduced into the sampling needle 10. The sample holding part 17 includes attaching parts 21, 22, and a flexible part 26. The outer diameters of the attaching parts 21 and 22 are arranged to be larger than the outer diameter of the flexible part 26. In one specific example, the outer diameters of the attaching parts 21 and 22 may be set to 1.6 mm, and the outer diameter of the flexible part 26 may be set to 1.0 mm. Also, in a preferred embodiment, the outer diameter of the sampling part 16 is arranged to be substantially equal to the outer diameter of the flexible part 26 (e.g., 1.0 mm).

As is shown in FIG. 6, the attaching part 21 is attached to the holder 24. The holder 24 is connected to a moving mechanism (not shown) that is configured to move the sampling needle 10. The holder 24 includes a main body part 24A and a screw part 24B and is fixed by screwing the screw part 24B to the main body part 24A. It is noted that a moving force is applied to the holder 24 by the moving mechanism upon moving the sampling needle 10, and thereby the attaching part 21 is preferably arranged to be relatively rigid. Accordingly, the outer diameter of the attaching part 21 is arranged to be greater than those of the sampling part 16 and the flexible part 26.

The attaching part 22, which is arranged at the other end of the sampling needle 10 on the opposite side of the tip portion 23, is attached to the injection valve 15 as is shown in FIG. 7. Therefore, the attaching part 22 is preferably arranged to be relatively rigid as well. Accordingly, the outer diameter of the attaching part 22 is also arranged to be greater than those of the sampling part 16 and the flexible part 26. By arranging the outer diameters of the attaching parts 21 and 22 to have relatively large diameters, attachment of the sampling needle 10 to the needle moving mechanism and the injection valve 15 may be improved, and the points of attachment at the sampling needle 10 may be prevented from being damaged.

As is described above, in a preferred embodiment, the outer diameters of the sampling part 16 and the flexible part 26 are arranged to be equal. However, the lengths of the sampling part 16 and the flexible part 26 are arranged to differ. In one specific example, the length of the sampling part 16 may be 75 mm, and the length of the flexible part 26 may be 485 mm. In this case, the length of the flexible part 26 is approximately 6.5 times the length of the sampling part 16.

In such an arrangement, even if the outer diameters of the sampling part 16 and the flexible part 26 have equal outer diameters, the sampling part 16 has higher rigidity than the flexible part 26, and thereby, the sampling part 16 may be prevented from deforming upon being inserted into ports such as the injection port 19. The flexible part 26, which is longer than the sampling part 16, may be flexibly deformed so that even when the attaching part 21 is moved by the needle moving mechanism while the attaching part 22 is fixed to the injection valve 15, the sampling part 16 may be accurately moved to a predetermined port.

It is noted that the sampling part 16 and the sample holding part 17 are preferably arranged into a seamless structure. In this case, a seam line is not created between the sampling part 16 and the sample holding part 17. Also, the inner diameters of the sampling part 16 and the sample holding part 17 are arranged to be equal. In one specific example, the inner diameter of the sampling needle 10 may be 0.55 mm throughout its length.

In a preferred embodiment, the sampling part 16 and the sample holding part 17 may be arranged into a seamless structure by using a seamless tube as the sampling needle 10 (the sampling part 16 and the sample holding part 17). The seamless tube may be fabricated by creating a hole in a material (e.g., stainless steel) to form a tube having a relatively thick wall (hollow material), and then rolling and die processing the hollow material to create a fine tube.

As can be appreciated from the above descriptions, in the sampling needle 10 according to the present embodiment, no seam line is created between the sampling part 16 and the sample holding part 17, and thereby the border region between the sampling part 16 and the sample holding part 17 may be smooth and continuous. Also, by arranging the inner diameters of the sampling part 16 and the sample holding part 17 to be equal, a step portion is not created at the border region between the sampling part 16 and the sample holding part 17.

In the present embodiment, portions at which a sample may be prone to remain within the sampling needle 10 (i.e., portions that may cause a change in the flow of a sample upon its introduction or discharge) are not created, and thereby, a sample may be prevented from remaining within the sampling needle 10. In turn, the occurrence of carry-over may be prevented, and the measuring accuracy may be improved in a measuring apparatus such as the liquid chromatography apparatus using the sampling needle 10 of the present embodiment.

In the following, operations of the sample injection apparatus 1 that includes the sampling needle 10 according to an embodiment of the present invention and a method of injecting a sample are described with reference to FIG. 7.

According to the present embodiment, first, the sampling needle 10 that is cleaned in advance is moved to the sample container 14 by the needle moving mechanism, and is inserted into a sample that is supplied in the sample container 14. Then, the syringe 11 connected to the sampling needle 10 is pulled so that the sample is suctioned from the sample container 14 and introduced into the sampling needle 10.

After suctioning of the sample is performed, the sampling needle 10 is moved to the cleaning port 20 by the needle moving mechanism and the sampling needle 10 is inserted into the cleaning liquid supplied in the cleaning port 20. In one embodiment, pure cleaning liquid may be continually supplied to the cleaning port 20, and the outer wall of the sampling needle 10 may be cleaned at the cleaning port 20. In this case, an ultrasonic transducer is connected to the cleaning port 20 to oscillate the cleaning port 20 upon performing the cleaning process. In this way, high cleaning efficiency may be achieved.

After cleaning the sampling needle 10, the needle moving mechanism is used to insert the sampling needle 10 into the injection port 19 of the injection valve 15. Then, the syringe 11 connected to the sampling needle 10 is pushed so that the sample extracted within the sampling needle 10 may be injected into the injection port 19.

Upon discharging the sample from the sampling needle 10, since a seam line does not exist between the sampling part 16 and the sample holding part 17 of the sampling needle 10, and the inner diameters of the sampling part 16 and the sample holding part 17 are arranged to be equal, the sample may be prevented from remaining within the sampling needle after the sample is discharged therefrom. In this way, the occurrence of carry-over may be prevented.

Figure 8:
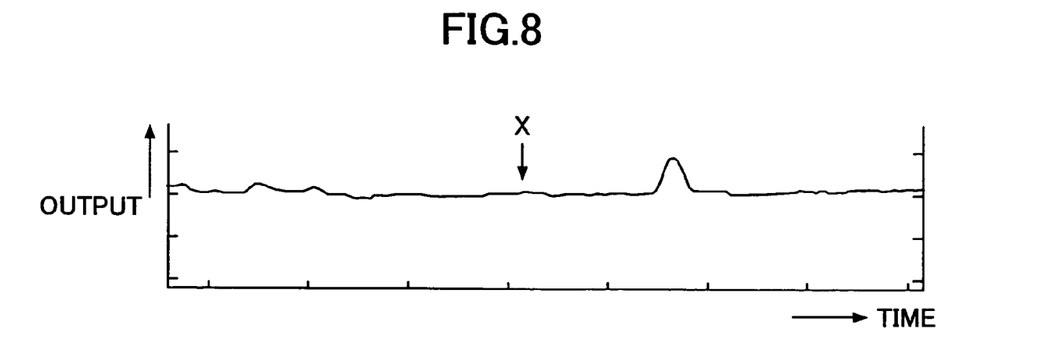
FIG. 8 is a graph illustrating an advantageous effect obtained by using the present embodiment.

FIG. 8 is a graph indicating measurement results obtained by injecting a blank sample solution (mobile phase) into the sample injection apparatus 1 after the sample injection process as is described above was completed to determine whether traces of the previous sample solution may be found in the blank sample solution. It may be appreciated from this drawing that by using the sampling needle 10 according to an embodiment of the present invention, a carry-over peak is prevented from occurring at the point indicated by arrow X at which carry-over usually occurs (see FIG. 4). Thus, it may be construed that the occurrence of carry-over may be prevented by using the sampling needle 10 and the injection apparatus 1 according to embodiments of the present invention.

Further, it is noted that the present invention is not limited to the specific embodiments described above, and variations and modifications may be made without departing from the scope of the present invention.

The present application is based on and claims the benefit of the earlier filing date of Japanese Patent Application No. 2004-331987 filed on Nov. 16, 2004, the entire contents of which are hereby incorporated by reference.

What is claimed is:

1. A sampling needle comprising:
   a sampling part that is inserted into a sample; and
   a sample holding part that holds the sample introduced through the sampling part;
   wherein the sampling part and the sample holding part are arranged into a seamless structure;
   an inner diameter of the sampling part and an inner diameter of the sample holding part are equal; and
   wherein the sample holding part includes an attaching part that is fixed to an external apparatus. and a flexible part that is configured to flexibly deform, and wherein an external diameter of the flexible part being smaller than an external diameter of the attaching part.

2. The sampling needle as claimed in claim 1, wherein the sampling part and the sample holding part are integrally arranged into a seamless tube.

3. A sample injection apparatus that is used in a testing apparatus and is configured to automatically inject a sample into the testing apparatus, the sample injection apparatus comprising:
   a sampling needle that includes a sampling part that is inserted into a sample, and a sample holding part that holds the sample that is introduced through the sampling part;
   wherein the sampling part and the sample holding part are arranged into a seamless structure;
   an inner diameter of the sampling part and an inner diameter of the sample holding part are equal; and
   wherein the sample holding part includes an attaching part that is fixed to an external apparatus, and a flexible part that is configured to flexibly deform, and wherein an external diameter of the flexible part being smaller than an external diameter of the attaching part.

* * * * *